Jan. 29, 1974 B. J. MACHIN ET AL Plant Pat. 3,455
CHRYSANTHEMUM PLANT
Filed May 12, 1972
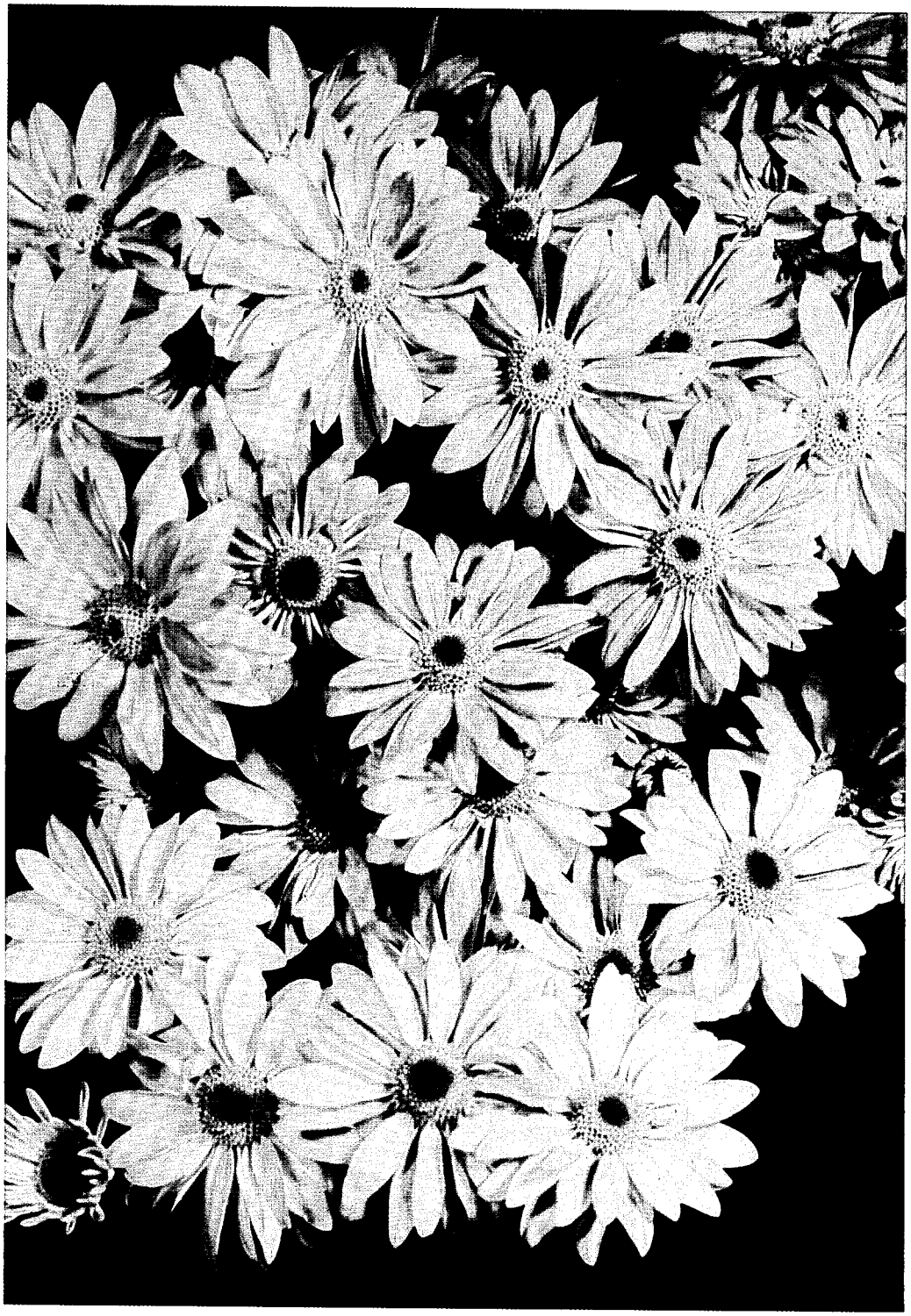

United States Patent Office

Plant Pat. 3,455
Patented Jan. 29, 1974

3,455

CHRYSANTHEMUM PLANT

Barrie J. Machin, Chichester, and G. B. Hall, Ashley Green, Chesham, England, assignors to Yoder Brothers, Inc., Barberton, Ohio

Filed May 12, 1972, Ser. No. 252,949
Int. Cl. A01h *5/00*
U.S. Cl. Plt.—74 1 Claim

The present invention comprises a new and distinct cultivar of daisy form chrystanthemum plant which is a sport of the unpatented cultivar Apricot Marble, which is in turn a sport of an unpatented cultivar well-known commercially in the United States as Pink Marble.

The new cultivar is similar in many respects to Pink Marble, having the same characteristics of:

(1) Plant habit.
(2) Recommended period of flowering.
(3) Daisy flower form.
(4) Foliage color, shape and size.

The new cultivar is distinguished from Pink Marble by the following characteristics:

(1) Flowers approximately one-quarter inch larger.
(2) Best flower form of any sport in the Marble family, having a very flat symmetrically petalled flower with no twisting or reflexing of the petals.
(3) A rose pink flower color.
(4) Approximately two inches more vigor.

The new cultivar was found in a flowering block of the parent Apricot Marble at Ashley Green, Chesham, Buck, England, and when asexually reproduced by cuttings at Chichester, Sussex, England, has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, daylength and light intensity. Suggested flowering in the northern and western United States is from May through October; in coastal California, January through December, and in Florida, December through April.

The accompanying drawing shows the unique characteristics of the new cultivar, the color being as nearly true as possible with color photographs of this type. In the photographic drawing, three cultivars are illustrated for comparison purposes, with Pink Marble appearing on the bottom of the photograph; Blue Marble, an unpatented but commercially well-known cultivar, at the upper right, and the new cultivar at the upper left.

In the description which follows, flower color references are made to the Ridgway Color Book, 1912 edition, and foliage color references are made to the Munsell Color Book, 1963 edition. Comparisons are made with the cultivar Pink Marble. Where only a single value or description appears for the new cultivar, the same value or description applies also to the comparison cultivar Pink Marble.

Botanical classification: *Chrysanthemum morifolium*

| | Coral Marble | Pink Marble |
|---|---|---|
| Bloom: | | |
| Size | Approximately 2¾″ | Approximately 2½″. |
| Fully expanded | Approximately 3¼″ | Approximately 3″. |
| Borne | In compound lateral clusters of 5 to 8 flowers | |
| Stems | Wiry | |
| Form | Daisy | |
| Permanence | 7 days | |
| Color: | | |
| Center of flower | Kildare green, to primaline yellow, XVI 19′ | Kildare green, to primaline yellow, XVI 19′. |
| Base of petals | Strontian yellow, XVI 23′ | Dull green-yellow, XVII 27′. |
| Inside of petals | Corinthian red, XXVII 3″ to pale vinaceous XXVII 1″f | Laelia pink, XXXVIII 67″d to pale vinaceous lilac, XLIV 69″. |
| Reverse of petals | Shell pink, XXVII 11″f to seashell pink, XIV 11′f | Mauvette, XXV 65′f. |
| Tonality from a distance | Vinaceous, XXVII 1″d | Light pinkish lilac, XXXVII 65″f. |
| Discoloration | Pale vinaceous, XXVII 1″f | Pale vinaceous lilac, XLIX 69″. |
| Petals: | | |
| Texture | Smooth | |
| Appearance & form | Open at base broad at mid-point, tapering to a blunt point | |
| Arrangement | Composite, whorled, on a single receptacle | |
| Persistence | Resist shatter | |
| Fragrance | Typical chrysanthemum | |
| Reproductive organs: | | |
| Stamen, anthers | 200–250 | |
| Pollen | Abundent to none (functional sterility) | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Upright† | |
| Height | Approximately 44″–49″, given 3–5 long day weeks and 12 to 14 weeks total crop time as designated in the timetables of Yoder Brothers, Inc., Barberton, Ohio. | Approximately 42″–47″, give 3–5 long day weeks and 12 to 14 weeks total crop time as designated in the timetables of Yoder Brothers, Inc., Barberton, Ohio. |
| Spread | None when grown single stem to moderate when pinched | |
| Foliage: | | |
| Top side | Dark green, 7.5GY¾ | |
| Size | 5¾″ long, 3¼″ wide | |
| Quantity | Numerous | |
| Shape | Spatulate lobed | |
| Texture | Smooth | |
| Ribs & veins | Prominent | |
| Edge | Moderately indented | |
| Serration | Moderate | |
| Under side | Light green, 7.5GY5/4 | |
| Stipules | Prominent | |

We claim:

1. A new and distinct cultivar of chrysanthemum characterized particularly as to its uniqueness when compared to the cultivar Pink Marble by its aproximately one-quarter inch larger flower, its very flat symmetrically petalled flowers which have no twisting or reflexing of the petals, its rose pink flower color, and approximately two inches more vigor.

No references cited.

ROBERT E. BAGWILL, Primary Examiner

UNITED STATES PATENT OFFICE
CERTIFICATE OF CORRECTION

Patent No. 3,455 Dated January 29, 1974

Inventor(s) BARRIE J. MACHIN and G. B. HALL

It is certified that error appears in the above-identified patent and that said Letters Patent are hereby corrected as shown below:

In the description below Columns 1 and 2, opposite "Foliage:" and opposite "Top side", the description should read --Dark green, 7.5GY3/4--, instead of "Dark green, 7.5GY¾".

Signed and sealed this 1st day of October 1974.

(SEAL)
Attest:

McCOY M. GIBSON JR.
Attesting Officer

C. MARSHALL DANN
Commissioner of Patents